(12) United States Patent
Ferrari et al.

(10) Patent No.: US 9,469,843 B2
(45) Date of Patent: Oct. 18, 2016

(54) CAROTENOID EXTRACTION FROM PLANT MATERIAL

(75) Inventors: Davide Ferrari, Parma (IT); Antonio Aldini, Parma (IT); Stefano Cuccolini, Reggio Emilia (IT)

(73) Assignee: John Bean Technologies S.p.A., Parma (IT)

( * ) Notice: Subject to any disclaimer, the term of this patent is extended or adjusted under 35 U.S.C. 154(b) by 622 days.

(21) Appl. No.: 13/250,956

(22) Filed: Sep. 30, 2011

(65) Prior Publication Data
US 2013/0085309 A1    Apr. 4, 2013

(51) Int. Cl.
| | | |
|---|---|---|
| *C12N 9/00* | (2006.01) | |
| *C07C 11/21* | (2006.01) | |
| *C07C 403/24* | (2006.01) | |
| *A23L 1/30* | (2006.01) | |
| *C12P 23/00* | (2006.01) | |

(52) U.S. Cl.
CPC .............. *C12N 9/00* (2013.01); *A23L 1/3002* (2013.01); *C07C 11/21* (2013.01); *C07C 403/24* (2013.01); *C12P 23/00* (2013.01); *C12Y 302/01004* (2013.01); *C07C 2101/16* (2013.01); *Y02P 20/52* (2015.11)

(58) Field of Classification Search
CPC .................. A23V 2002/00; A23V 2200/332; A23V 2250/21162; A23V 2250/211; A23V 2200/224; A23V 2250/156; A23V 2250/186; A23V 2250/2108; A23V 2250/61; A23V 2250/7042; A23V 2250/7044; A23V 2250/7052; A23V 2250/18; A61K 2300/00
See application file for complete search history.

(56) References Cited

U.S. PATENT DOCUMENTS

| | | | |
|---|---|---|---|
| 3,206,316 A | 9/1965 | Klaui | |
| 7,557,146 B2 * | 7/2009 | Sabio Rey | 514/762 |
| 2003/0180435 A1 * | 9/2003 | Shi | 426/615 |
| 2006/0058269 A1 * | 3/2006 | Lockwood et al. | 514/124 |
| 2007/0122363 A1 * | 5/2007 | Giniger et al. | 424/58 |

FOREIGN PATENT DOCUMENTS

| | | |
|---|---|---|
| FR | 2219965 A | 9/1974 |
| WO | 97/15554 A1 | 5/1997 |

OTHER PUBLICATIONS

International Search Report mailed Feb. 12, 1997, issued in International Application No. PCT/HU96/00057, filed Oct. 8, 1996, 3 pages.

* cited by examiner

*Primary Examiner* — Blaine Lankford
(74) *Attorney, Agent, or Firm* — Christensen O'Connor Johnson Kindness PLLC

(57) ABSTRACT

A method of extracting carotenoids from plant material generally includes acquiring plant material including carotenoids, treating the carotenoids with a first enzyme to create a first enzyme treated mixture, wherein the first enzyme includes cellulase, and separating the first enzyme extracted carotenoids from the first enzyme treated mixture. Natural carotenoid concentrate obtained from plant material are also provided.

16 Claims, 1 Drawing Sheet

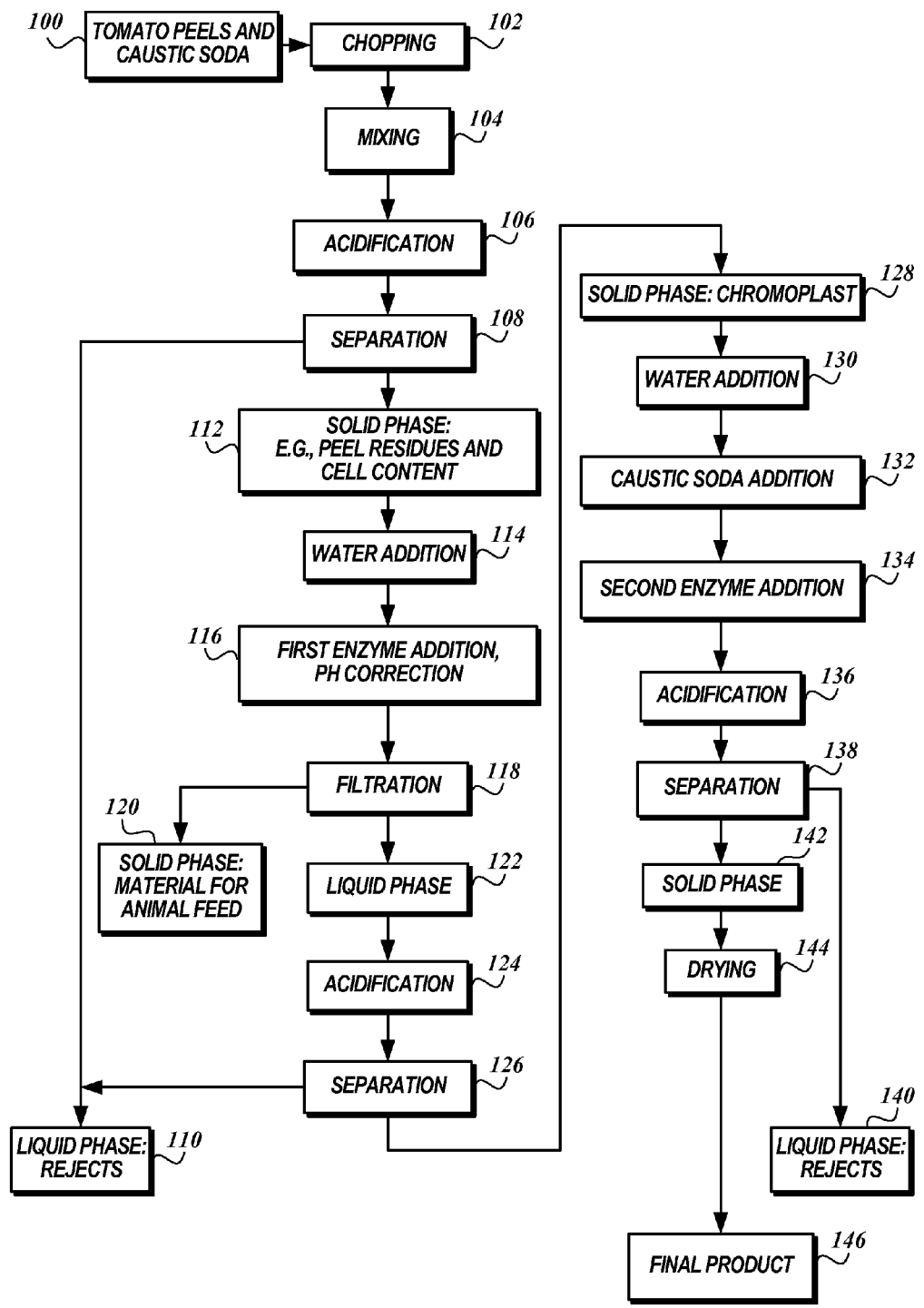

CAROTENOID EXTRACTION FROM PLANT MATERIAL

BACKGROUND

Carotenoids are referred to herein as a group of unsaturated hydrocarbons containing isoprene units or their derivatives substituted by various functional groups in lipid addition compounds of the same (i.e., prenyl-lipids). Carotenoids include, but are not limited to lycopene, beta-carotene, alpha-carotene, xanthophyll, etc.

A healthy diet involves the consumption of appropriate amounts of high quality fruits and vegetables, of which carotenoids are essential components. For example, carotenoids, such as lycopene and beta-carotene, are highly effective antioxidants and may also have provitamin functions. In fact, diets rich in these carotenoids are recognized as reducing the risks of various diseases, including prostate cancer and cardiovascular disease.

In previously developed carotenoid extraction methods, lipophilic solvents are used, including both toxic and non-toxic solvents. Toxic solvents (such as hexane and chlorinated hydrocarbons) can leave trace residues that migrate and accumulate in target cells and tissues. Non-toxic solvents (such as ethanol, rectified alcohol, and isopropyl alcohol), although non-toxic, are also disadvantageous in food processing. These solvents not only create flammability and explosion safety hazards in the food processing plant in which they are used, but also require disclosure of solvent content in the final product.

In view of the advantageous effects of the consumption of carotenoids and the drawbacks of the previously developed extraction methods, there exists a need for improved methods to extract carotenoids from plant material for consumption.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a method of extracting carotenoids from plant material is provided. The method generally includes acquiring plant material including carotenoids, treating the carotenoids with a first enzyme to create a first enzyme treated mixture, wherein the first enzyme includes cellulase, and separating the first enzyme extracted carotenoids from the first enzyme treated mixture.

In accordance with another embodiment of the present disclosure, a method of extracting carotenoids from plant material is provided. The method generally includes acquiring plant material including carotenoids, treating the carotenoids with a first enzyme to create a first enzyme treated mixture, and treating the carotenoids with a second enzyme to create a second enzyme treated mixture, wherein the second enzyme is different from the first enzyme.

In accordance with another embodiment of the present disclosure, a natural carotenoid concentrate obtained from plant material. The concentrate generally includes lycopene content greater than about 60,000 ppm, and substantially no solvent residues.

DESCRIPTION OF THE DRAWINGS

The foregoing aspects and many of the attendant advantages of this disclosure will become more readily appreciated as the same become better understood by reference to the following detailed description, when taken in conjunction with the accompanying drawing, wherein:

The FIGURE is a process flow diagram of a carotenoid extraction method in accordance with one embodiment of the present disclosure.

DETAILED DESCRIPTION

In accordance with one embodiment of the present disclosure, a process for extracting carotenoids from plant material is provided. In general the process includes isolating the carotenoids that may be present in the chromoplasts and/or the chloroplasts of the plant material, separating the carotenoids into a carotenoid fraction, then cleaving cellulosic material and lipoproteins by enzymatic treatment of the carotenoid fraction, as described in greater detail below.

The process first includes acquiring the plant material. As a non-limiting example, tomato peels, which are generally thought to be waste in the food industry, can be used as a plant material. Other suitable plant materials may include carrots, peppers, watermelon, certain types of algae, etc.

Caustic Treatment

In one embodiment of the present disclosure, the plant materials are treated to be prepared for the extraction process. To dissolve the carotenoid fraction and create a dissolved carotenoid mixture, caustic soda is added to achieve a basic pH in the mixture, as represented in block 100 of the illustrated process in the FIGURE. In one embodiment of the present disclosure, a caustic agent is added in an amount in the range of about 0.5 N to about 2 N, achieving a pH in a range of about 10 to about 14. In another embodiment, the caustic agent is added in an amount in the range of about 1 N to 1.5 N. As a non-limiting example, the caustic agent is added in amount of about 1 N. In another embodiment, the pH of the mixture is in the range of about 11 to about 13. In another embodiment, the pH of the mixture is greater than 11. In another embodiment, the pH is greater than 8.5. Suitable caustic agents may include NaOH, KOH, and other caustic agents suitable for food processing.

The caustic agent concentration used in embodiments of the present disclosure is in a range that is higher than typically used with previous prior art processes (pH 8.5), for example, as described in PCT International Publication No. WO 97/15554, to Koch et al., the disclosure of which is hereby expressly incorporated by reference. In that regard, the inventors found that a higher pH allows for a higher yield recovery of the carotenoid fraction from the plant material. For example, as described in greater detail in EXAMPLE 2 below, experimental analysis shows a significant increase in concentration between samples treated with 1 N caustic soda, compared with samples treated to a pH of 8.5 or not treated with caustic soda.

After caustic soda has been added, the plant materials are chopped, ground, milled fiberized, and/or refined, and then mixed for an appropriate time and at an appropriate temperature, as represented in blocks 102 and 104 of the illustrated process in the FIGURE. Suitable mixing times and temperature ranges may be in the range of about 1.5 to about 2.5 hours and about 65° C. to about 75° C. As a non-limiting example, the plant materials are mixed at about 70° C. for about 2 hours.

First Precipitation of the Solid Fraction

After mixing with caustic soda and creating the dissolved carotenoid mixture, the treated mixture is acidified to an acidic pH in one embodiment of the present disclosure, as represented in block 106 of the illustrated process in the FIGURE. Acidification results in the coagulation of proteins that are linked to the carotenoids to precipitate a solid carotenoid fraction from the mixture. The inventors advantageously found that proteins coagulate better at a pH lower than 4. Of note, a pH of 4 has been commonly used in other carotenoid extraction processes, for example, as described in PCT International Publication No. WO 97/15554, to Koch et al., the disclosure of which is hereby expressly incorporated by reference.

In embodiments of the present disclosure, suitable ranges for the acidic pH include less than about 4, about 1 to about 4, and about 2 to about 3. As a non-limiting example, the mixture is acidified to a pH of 2.2.

First Centrifuge Separation of Solid Fraction

In another embodiment of the present disclosure, the solid fraction may be separated using a centrifuge separation process after acidification, as represented in block 108 of the illustrated process in the FIGURE. The liquid phase is rejected, as represented in block 110. The solid phase including peel residues and cell content continues through the process, as represented in block 112.

First Enzymatic Treatment

After separation of the solid fraction, water may be added to the mixture to re-dilute the mixture, in another embodiment of the present disclosure, as represented in block 114 of the illustrated process in the FIGURE. In another embodiment, an enzyme is added to the diluted mixture with a pH correction to a pH level specific for the enzyme (e.g., cellulase and cellulase mixtures) to be used in the enzymatic treatment step, as represented in block 116, to create a first enzyme treated mixture.

As a non-limiting example, a suitable enzyme is at least one cellulose hydrolyzing enzyme, such as cellulase (or a mixture of cellulases). Cellulase refers to a class of enzymes produced, for example, by fungi, bacteria, and protozoans that catalyze the hydrolysis of cellulose. Although not wishing to be bound by theory, the inventors believe that plant material, such as tomato peels, includes fibrous material that is similar to cellulosic material. Therefore, cellulase is used for enzymatic cleavage to extract carotenoids in accordance with embodiments of the present disclosure.

The pH is corrected when the first enzyme (cellulase and cellulase mixtures) is added to conform the mixture to optimal operating conditions for the first enzymatic treatment. In accordance with embodiments of the present disclosure, suitable pH, treatment times, and temperature ranges for the enzymatic treatment may be in the range of pH of about 4 to about 5, time of about 4 to about 6 hours, and temperature of about 45° C. to about 55° C. In one non-limiting example, the pH of the mixture is corrected to 4.2, and enzymatic treatment is for about 4-6 hours at about 50° C.

In one embodiment of the present disclosure, a suitable concentration for cellulase may be in the range of about 2% to about 6% of the quantity of solid phase (see block 112) before water and enzyme addition. In another embodiment, the cellulase concentration is about 3% to about 4% of the quantity of solid phase (see block 112) before water and enzyme addition.

These concentration ranges were established based on experimental data, as detailed below in EXAMPLES 3 and 5. In that regard, the yield achieved with enzyme concentration of 3% is significantly higher the yield achieved with enzyme concentration of 2.15%. In addition, lycopene concentration also increases with an increase in enzyme concentration (see EXAMPLE 3). Little difference was shown in lycopene extraction yield and concentration between enzyme concentration of 3% and enzyme concentration of 6% (see EXAMPLE 5).

In another embodiment of the present disclosure, cellulase enzymatic treatment may also be combined with another enzyme during the enzymatic treatment process. For example, one non-limiting example of enzyme combination is the combination of cellulase and pectinase in one process step. Pectinase is a general term for enzymes, such as pectolyase, pectozyme, and polygalacturonase, commonly referred to as pectic enzymes. Pectic enzymes break down pectin, a polysaccharide substrate that is found in the cell walls of plants.

In accordance with one embodiment, a suitable concentration for the combined enzyme mixture may be in the range of about 4% to about 12% of the quantity of solid phase (see block 112) before water and enzyme addition. In another embodiment, the combined concentration is about 6% to about 8% of the quantity of solid phase (see block 112) before water and enzyme addition. In the case of combining cellulase and pectinase, the working pH range is substantially similar to the optimal pH range for cellulase alone. In one non-limiting example, cellulase and pectinase are each added to the mixture at about 3% of the quantity of solid phase before water and enzyme addition and at a pH of about 4.5.

The results show that a combined cellulase and pectinase first enzyme treatment step improve yield compared to a first enzyme treatment step only using cellulase (see EXAMPLE 7).

As described in detail below, whether the first enzymatic treatment step is a single enzyme or a combined enzyme treatment step, it should be appreciated that the process may still include a second enzymatic treatment step. In fact, the results show that the protease enzymatic treatment step, in addition to a cellulase enzymatic treatment step, increases lycopene concentration in the final product, but decreases yield (see EXAMPLES 4 and 8).

Filtration

In another embodiment of the present disclosure, the solid phase of the mixture is filtered from the liquid phase using a filtration system, such as a centrifugal extractor having a 100 micron screen, after completion of the enzyme digestion, as represented in block 118 of the illustrated process in the FIGURE. The solid phase is rejected and may be used as material for animal feed, as represented in block 120. The liquid phase continues in the processing, as represented in block 122.

The carotenoids are substantially contained in the chromoplasts of the cell material of the plant material, and the chromoplasts tend to attach to fibers. The inventors discovered that a centrifuge process after enzymatic treatment, as commonly used in previously developed process, tends to separate the fibers (having a low carotenoid fraction) and its attached chromoplasts (having a high carotenoid fraction) as solid material rejects. In the alternative, a filtration process as used in the present disclosure, allows for fibers of a certain small size (together with attached chromplasts) to pass through the screen such that lycopene can continue to be extracted from the chromoplasts. However, larger fibers (such as peel residue) do not pass through the screen and are therefore rejected.

Therefore, by using a filtering process, as opposed to a centrifuge process, after enzymatic treatment, extracted lycopene concentration and yield of the final product may be improved.

Second Precipitation of the Solid Fraction

In another embodiment of the present disclosure, as the liquid phase continues in the process, it is acidified back to a low pH to again precipitate a solid carotenoid fraction from the mixture, as represented in block 124 of the illustrated process in the FIGURE. In other embodiments of the present disclosure, suitable ranges for the acidic pH include less than about 4, in the range of about 1 to about 4, and in the range of about 2 to about 3. As a non-limiting example, the mixture is acidified to a pH of 2.2.

Second Centrifuge Separation

After the carotenoid fraction has been precipitated, the mixture can be centrifuged for separation in another embodiment of the present disclosure, as represented in block 126. The liquid phase is the rejected portion, as represented in block 110, and the solid phase continuing through the process, as represented in block 128.

Second Enzymatic Treatment

In another embodiment, water is added to the mixture to re-wet the mixture, as represented in block 130 of the illustrated process in the FIGURE. In another embodiment, the pH is corrected to conform the mixture to optimal operating conditions for the second enzymatic treatment (e.g., protease and protease mixtures) (see block 134). For example, in one embodiment of the present disclosure, caustic soda is added up to a pH in the range of about 9 to about 10 (see block 132). As a non-limiting example, the pH is raised to 9.5.

In another embodiment, proteolitic enzyme is added after pH adjustment. Suitable treatment times and temperature ranges for the enzymatic treatment may be in the range of time of about 2.5 to about 3.5 hours, and temperature of about 55° C. to about 60° C. As a non-limiting example, the enzyme treatment may be for about 3 hours at 58° C.

The purpose of the second enzyme treatment is to partially or totally cut proteins linked to carotenoids in amino acids and peptides create a second enzyme treated mixture. In that regard, the second enzyme may include protease, which is any enzyme that conducts proteolysis, i.e., that begins protein catabolism by hydrolysis of the peptide bonds that link amino acids together in the polypeptide chain forming the protein. As another non-limiting example, pancreatin may be substituted for protease. Pancreatin is a mixture of several digestive enzymes produced by the exocrine cells of the pancreas, including amylase, lipase, and protease.

As mentioned above, the results show that the protease enzymatic treatment step, in addition to a cellulase enzymatic treatment step, significantly increases lycopene concentration in the final product (see block 146), but decreases yield (see EXAMPLES 4 and 8). While not wishing to be bound by theory, it is believed by the inventors the caustic treatment and cellulase enzyme treatment steps help to "break" or "open up" the plant cells, which then allows for a more effective protease enzyme treatment step. Therefore, it may be advantageous to treat the plant material with a cellulase enzyme (or cellulase mixture) prior to treating the plant material with a protease enzyme (or protease mixture) in the process. However, it should be appreciated that in some embodiments of the present disclosure, the protease enzyme treatment step may precede the cellulase enzyme treatment step.

Third Precipitation of the Solid Fraction

In another embodiment of the present disclosure, the liquid phase continues in the process and is acidified back to a low pH to again precipitate a solid carotenoid fraction from the mixture, as represented in block 136 of the illustrated process in the FIGURE. In other embodiments of the present disclosure, suitable ranges for the acidic pH are less than about 4, about 1 to about 4, and about 2 to about 3. As a non-limiting example, the mixture is acidified to a pH of 2.2.

Third Centrifuge Separation

In another embodiment, after the carotenoid fraction has been precipitated, the mixture can be centrifuged for separation, as represented in block 138. The liquid phase is the rejected portion, as represented in block 140, and the solid phase continues through the process, as represented in block 142. The solid phase then continues to a drying process, as represented in block 144, which becomes the final product, as represented in block 146.

In one embodiment of the present disclosure, a suitable final product has less than 15% water content with a carotenoid content of greater than 60,000 ppm. If the plant material used in the process is tomato peels, a suitable final product has less than 15% water content with a lycopene content of greater than 60,000 ppm.

No Solvent Extraction

As mentioned above, previously designed carotenoid extraction processes lipophilic solvents have been used, including both toxic and non-toxic solvents, to further extract carotenoids from plant material. Toxic solvents include, but are not limited to, hexane and chlorinated hydrocarbons; non-toxic solvents include, but are not limited to, ethanol, rectified alcohol, and isopropyl alcohol, as described in PCT International Publication No. WO 97/15554, to Koch et al., the disclosure of which is hereby expressly incorporated by reference. Embodiments of the present disclosure do not include the use of lipophilic solvents in the extraction processes described herein. Therefore, the final carotenoid composition also does not include any solvent content.

EXAMPLES

Various experiments were conducted to study the effect of process variables with respect to concentration and extraction yield in the final output product. Of note, yield data is expressed in percentage and represents the lycopene quantity extracted compared to lycopene originally present in the raw material (tomato peels). Concentration data is expressed in parts-per-million (ppm) per dry substance. The tomato peels were obtained from tomatoes purchased at the supermarket having a lycopene yield of 100% and a concentration of about 2700-4500 ppm.

Of note, the high variability in the data could be a result of a non-homogenous raw material. It is believed that homogeneity may be improved by introducing a fine-milling step for the tomato peels.

Statistical evaluations of data were performed using a T-student test with 95% confidence.

Example 1

Lycopene Extraction Process

Referring to the FIGURE, an exemplary process for lycopene extraction is shown. The specific details of the process are as follows.

First, the tomato peels were obtained, and caustic soda was added at a level of 1 N, as represented in block 100. The tomato peels were chopped, as represented in block 102. The mixture was maintained at 70° C. for 2 hours, as represented in block 104. The mixture was then acidified to pH 2.2 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture at a concentration of 3% of the quantity of solid phase (see block 112) before water and enzyme addition, with pH correction to 4.2, which was mixed for 4 hours at 50° C., as represented in block 116. The mixture was then filtered using a centrifugal extractor having a 100 micron screen, with the solid phase going to waste, as represented in blocks 118 and 120. The liquid phase was then acidified and passed to a centrifuge step, as represented in blocks 122, 124, and 126. After the centrifuge step, the liquid phase was rejected, as represented in block 110. The solid phase from block 128 was diluted and caustic sold was added up to pH 9.5, as represented in blocks 130 and 132. Proteolitic enzymatic treatment was then initiated for 3 hours at a temperature in the range of 50-60° C., as represented in block 134. The mixture was acidified to pH 2.2, and centrifuged, as represented in blocks 136 and 138, to obtain a solid phase (see block 142) for drying (see block 144).

The resulting lycopene power includes about 6% lycopene (about 60,000 ppm), about 52% carbohydrates, about 13.3% fibers, about 2.5% lipids, about 3.2% ash, about 13% proteins, and about 10% water. Although not measured, beta-carotene content is expected to be about 5-10% of the lycopene content.

Example 2

Effects of Caustic Soda

Tests were performed to determine the effect of caustic soda concentration and the presence or absence of cellulase enzyme used in a lycopene extraction process from tomato peels. In particular, these two variables were studied with respect to concentration and extraction yield in the final output product.

Three levels of caustic soda concentration were studied: Soda 1 (no soda); Soda 2 (soda addition to pH 8.5); and Soda 3 (soda addition up to 1N concentration). Two levels of enzyme concentration were studied: Enzyme 1 (no enzyme); and Enzyme 2 (cellulose enzyme at 1% concentration per the quantity of water used to dilute the enzyme).

The tomato peels were processed as follows and with reference to the exemplary process represented in the FIGURE. First, the tomato peels were obtained, and caustic soda was added in accordance with three different levels (no soda, pH 8.5, and 1 N), as represented in block 100. The tomato peels were chopped, as represented in block 102. The mixture was maintained at 70° C. for 2 hours, as represented in block 104. The mixture was then acidified to pH 4 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture at two different levels of concentration (no enzyme and 1%), with pH correction to 4.5, which was mixed for 4 hours at 50° C., as represented in block 116. The mixture was then filtered using a centrifugal extractor having a 100 micron screen, with the solid phase going to waste, as represented in blocks 118 and 120. The liquid phase was passed to a centrifuge step, as represented in blocks 122 and 126. After the centrifuge step, the liquid phase was rejected, as represented in block 110, and the solid phase, as represented in block 128, was processed for lycopene concentration and yield.

The results show that caustic soda concentration has a significant effect on the concentration of lycopene. For example, a significant difference can be seen between samples treated with Soda 3 (soda addition up to 1N concentration), 40884 ppm, samples treated with Soda 2 (pH 8.5), 32432 ppm, and samples treated with Soda 1 (no soda), 22345 ppm.

TABLE 1

CONCENTRATION OF EXTRACTED LYCOPENE WITH CAUSTIC SODA VARIABLE IN PROCESS.

| Soda | Enzyme | Concentration Extracted Lycopene (ppm) | Std. Dev. | Number of Samples |
|---|---|---|---|---|
| 1.00 | 1.00 | 20359 | 782 | 3 |
|  | 2.00 | 23835 | 3035 | 4 |
|  | Total | 22345 | 2874 | 7 |
| 2.00 | 1.00 | 39920 | 11589 | 3 |
|  | 2.00 | 24944 | 4073 | 3 |
|  | Total | 32432 | 11298 | 6 |
| 3.00 | 1.00 | 46690 | 12181 | 3 |
|  | 2.00 | 35077 | 13856 | 3 |
|  | Total | 40884 | 13289 | 6 |

The results further show that enzyme treatment has a significant effect on yield. Samples treated with Enzyme 2 (enzyme at 1% concentration) achieved 54% yield, compared to samples treated with Enzyme 1 (no enzyme), which achieved only 19% yield.

TABLE 2

YIELD OF EXTRACTED LYCOPENE WITH ENZYME VARIABLE IN PROCESS.

| Enzyme | Soda | Yield Extracted Lycopene (%) | Std. Dev. | Number of Samples |
|---|---|---|---|---|
| 1.00 | 1.00 | 20 | 2.8 | 3 |
|  | 2.00 | 12 | 4.7 | 3 |
|  | 3.00 | 25 | 8.3 | 3 |
|  | Total | 19 | 7.6 | 9 |
| 2.00 | 1.00 | 51 | 3.9 | 4 |
|  | 2.00 | 73 | 7.3 | 3 |
|  | 3.00 | 40 | 15.3 | 3 |
|  | Total | 54 | 16.0 | 10 |

Example 3

Cellulase Enzyme Concentration and Duration of Treatment

To better understand the parameters for the cellulose enzyme process step, tests were performed on enzyme concentration and the duration of enzymatic treatment. Two levels of enzyme concentration were tested: Enzyme 1 (3% enzyme concentration per the sample weight prior to enzymatic treatment and water dilution); and Enzyme 2 (2.15% enzyme concentration per the sample weight prior to enzymatic treatment and water dilution). Two levels of enzymatic treatment duration were tested: Duration 1 (4 hours); and Duration 2 (6 hours).

The tomato peels were processed as follows and with reference to the exemplary process represented in the FIG- URE. First, the tomato peels were obtained, and caustic soda was added at a concentration of 1 N, as represented in block 100. The tomato peels were chopped, as represented in block 102. The mixture was maintained at 70° C. for 2 hours, as represented in block 104. The mixture was then acidified to pH 4 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture at two different concentrations (3% and 2.15%) and for two different durations (4 hours and 6 hours), with pH correction to 4.5, which was mixed for 4 hours at 50° C., as represented in block 116. The mixture was then filtered using a centrifugal extractor having a 100 micron screen, with the solid phase going to waste, as represented in blocks 118 and 120. The liquid phase was passed to a centrifuge step, as represented in blocks 122 and 126. After the centrifuge step, the liquid phase was rejected, as represented in block 110, and the solid phase, as represented in block 128, was processed for lycopene concentration and yield.

The results show that the concentration of the cellulose enzyme has a significant effect on lycopene yield achieved. Compare the yield achieved with Enzyme 1 (3%) of 71.88% with the yield achieved with Enzyme 2 (2.15%) of 40.03%.

In addition, lycopene concentration appears to increase with an increase in enzyme concentration. In that regard, 41500 ppm lycopene was achieved with Enzyme 1 (3%), compared to 35135 ppm with Enzyme 2 (2.15%). Although the results regarding lycopene concentration are not particularly significant, they do indicate interesting correlations that may require further study.

It appears that a longer duration of enzymatic treatment (e.g., 6 hours) reduces the yield and the concentration. Compare 41999 ppm after 4 hours of enzymatic treatment with 29726 ppm after 6 hours of enzymatic treatment. Also compare 71.88% yield after 4 hours of enzymatic treatment with 51.13% after 6 hours of enzymatic treatment.

Example 4

One Versus Two Enzyme Treatment Steps

In addition to cellulase enzyme treatment, the process further includes a protease enzyme treatment. Tests were conducted to determine the effect of the protease treatment step on the solid phase that is obtained after cellulase enzymatic treatment to determine if it is worthwhile to include both cellulase and protease enzymatic treatment steps in the overall process.

The tomato peels were processed as follows and with reference to the exemplary process represented in the FIGURE. First, the tomato peels were obtained, and caustic soda was added at a concentration of 1 N, as represented in block 100. The tomato peels were chopped, as represented in block 102. The mixture was maintained at 70° C. for 2 hours, as represented in block 104. The mixture was then acidified to pH 2.2 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture at 3% concentration, with pH correction to 4.5, which was mixed for 4 hours at 50° C., as represented in block 116. The mixture was then filtered using a centrifugal extractor having a 100 micron screen, with the solid phase going to waste, as represented in blocks 118 and 120. The liquid was corrected to pH 2.3, and passed to a centrifuge step, as represented in blocks 122, 125, and 126. After the centrifuge step, the liquid phase was rejected, as represented in block 110, and the solid phase for some samples, as represented in block 128, was processed for lycopene concentration and yield after cellulase enzymatic treatment.

In lieu of processing, for some samples additional process steps were performed to include a second enzymatic treatment step. In that regard, the solid phase from block 128 was diluted and caustic sold was added up to pH 9.5, as represented in blocks 130 and 132. Proteolitic enzymatic treatment was then initiated for 3 hours at a temperature in the range of 50-60° C., as represented in block 134. The mixture was then acidified to pH 2.2, and centrifuged, as represented in blocks 136 and 138, to obtain a solid phase (see block 142) after both cellulase and proteolytic enzymatic treatments.

The results show that the protease enzymatic treatment step increases lycopene concentration in the final product, but decreases yield. For example, the concentration of lycopene in the process immediately following cellulase enzymatic treatment is 33689 ppm, which compares with the concentration of lycopene in the process following the protease enzymatic treatment of 65,943 ppm, nearly doubling the concentration of lycopene. Regarding yield, lycopene yield immediately following cellulase enzymatic treatment is 64%, which compares with lycopene yield following the protease enzymatic treatment of 32%.

Example 5

Cellulase Enzyme Concentration

To further understand optimal cellulase enzyme concentration, two other levels of enzyme concentration were tested: Enzyme 1 (3% enzyme concentration per the sample weight prior to enzymatic treatment and water dilution); and Enzyme 2 (6% enzyme concentration per the sample weight prior to enzymatic treatment and water dilution).

The tomato peels were processed as follows and with reference to the exemplary process represented in the FIGURE. First, the tomato peels were obtained, and caustic soda was added at a concentration of 1 N, as represented in block 100. The tomato peels were chopped, as represented in block 102. The mixture was maintained at 70° C. for 2 hours, as represented in block 104. The mixture was then acidified to pH 2.2 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture at two different concentrations (3% and 6%), with pH correction to 4.5, which was mixed for 4 hours at 50° C., as represented in block 116. The mixture was then filtered using a centrifugal extractor having a 100 micron screen, with the solid phase going to waste, as represented in blocks 118 and 120. The liquid was corrected to pH 2.3, and passed to a centrifuge step, as represented in blocks 122, 125, and 126. After the centrifuge step, the liquid phase was rejected, as represented in block 110, and the solid phase, as represented in block 128, was processed for lycopene concentration and yield after cellulase enzymatic treatment.

The results show little difference in concentration and yield between Enzyme 1 (3%) and Enzyme 2 (6%). Compare concentration of 43969 ppm for Enzyme 1 (3%) and 34457 ppm for Enzyme 2 (6%). Also compare yield of 62% for Enzyme 1 (3%) and 69% for Enzyme 2 (6%).

Example 6

Elimination of One Centrifuge Step

The prior art process used four centrifuge steps in the process. To attempt to improve lycopene extraction yield and concentration, the process was run without the third centrifuge step.

The tomato peels were processed as follows and with reference to the exemplary process represented in the FIGURE. First, the tomato peels were obtained, and caustic soda was added at a concentration of 1 N, as represented in block 100. The tomato peels were chopped, as represented in block 102. The mixture was maintained at 70° C. for 2 hours, as represented in block 104. The mixture was then acidified to pH 2.2 and centrifuged, as represented in blocks 106 and 108. The liquid phase was rejected, as represented in block 110, and the solid phase was maintained for further processing and diluted with water, as represented in blocks 112 and 114. Cellulase enzyme was added to the mixture, with pH correction to 4.5, which was mixed for 4 hours at 50° C., as represented in block 116. The mixture was then filtered using a centrifugal extractor having a 100 micron screen, with the solid phase going to waste, as represented in blocks 118 and 120. The liquid was corrected to pH 2.3, and passed to a centrifuge step, as represented in blocks 122, 125, and 126. After the centrifuge step, the liquid phase was rejected, as represented in block 110. The solid phase from block 128 was diluted and caustic sold was added up to pH 9.5, as represented in blocks 130 and 132. Proteolitic enzymatic treatment was then initiated for 3 hours at a temperature in the range of 50-60° C., as represented in block 134. Some of the samples were centrifuged to remove excess water before the mixture was acidified to pH 2.2, and centrifuged, as represented in blocks 136 and 138, to obtain a solid phase (see block 142) for processing. Other samples were not centrifuged before the mixture was acidified to pH 2.2, thereby removing one centrifuge step.

The results show little difference in both concentration and yield. Compare a concentration of 65943 ppm lycopene without the third centrifuge step, and a concentration of 72026 ppm with the third centrifuge step. Also a yield of 32% without the third centrifuge step, and a yield of 36% with the third centrifuge step.

Example 7

Combined Enzymatic Treatment Step

To further understand enzymatic treatment, an enzymatic treatment step was performed using a combined mix of cellulase and pectinase enzymes. The total concentration of the enzyme was set at 3% in the cellulase only tests and a mixture of 3% cellulase and 3% pectinase tests.

The tomato peels were processed as follows and with reference to the exemplary process represented in the FIGURE. First, the tomato peels were obtained, and caustic soda was added in an amount of 1 N, as represented in block 100. The tomato peels were chopped, as represented in block 102. The mixture was maintained at 70° C. for 2 hours, as represented in block 104. The mixture was then acidified to pH 2.2 and centrifuged, as represented in blocks 106 and 108. The liquid phase was rejected, as represented in block 110, and the solid phase was maintained for further processing and diluted with water, as represented in blocks 112 and 114. An enzyme mixture was added to the mixture according to two different compositions (3% cellulase only and a mixture of 3% cellulase plus 3% pectinase), with pH correction to 4.2, which was mixed for 4 hours at 50° C., as represented in block 116. The mixture was then filtered using a centrifugal extractor having a 100 micron screen, with the solid phase going to waste, as represented in blocks 118 and 120. The liquid phase was acidified to pH 2.2 and then passed to a centrifuge step, as represented in blocks 122, 124, and 126. After the centrifuge step, the liquid phase was rejected, as represented in block 110, and the solid phase, as represented in block 128, was processed for lycopene concentration and yield.

The results show that combining cellulase and pectinase enzymes in the enzyme treatment step has a positive effect on yield. Compare a yield of only 61.9% with only cellulase enzyme, with a yield of 86.2% using combined enzymes. The concentration stays about the same. Compare a lycopene concentration multiplier of 14.2 with only cellulase enzyme, with concentration multiplier of 14.3 using combined enzymes.

Example 8

Whole Process Versus Partial Process

To further understand the lycopene extraction process, tests wee performed to compare the concentration of lycopene achieved by the entire process represented in the FIGURE with an abbreviated process through block 128 in the FIGURE.

The results show that samples obtained from the whole process have a significantly higher concentration value compared to samples through only a portion of the process (block 128). Compare lycopene concentration of 73,269 ppm (concentration multiplier of 22.8) for the whole process with lycopene concentration of 37,755 ppm (concentration multiplier of 11.9) for the partial process.

While illustrative embodiments have been illustrated and described, it will be appreciated that various changes can be made therein without departing from the spirit and scope of the disclosure.

The invention claimed is:

1. A method of extracting lycopene from plant material, the method comprising:
   (a) acquiring plant material including lycopene and treating the plant material with caustic soda in the range of about 0.5 N to about 2 N to substantially dissolve the lycopene and create a substantially dissolved lycopene mixture, wherein the pH of the substantially dissolved lycopene mixture is in the range of 10 to 14;
   (b) acidifying the substantially dissolved lycopene mixture to precipitate a solid lycopene fraction;
   (c) treating the solid lycopene fraction with a first enzyme and pH correction to create a first enzyme treated mixture, wherein the first enzyme includes cellulase;
   (d) separating the first enzyme extracted lycopene from the first enzyme treated mixture; and
   (e) treating the first enzyme solid phase treated mixture to substantially dissolve the lycopene and create a substantially dissolved first enzyme lycopene mixture, treating the first enzyme extracted lycopene with a second enzyme to create a second enzyme treated mixture, and separating the second enzyme extracted lycopene from the second enzyme treated mixture.

2. The method of claim 1, wherein acidifying the substantially dissolved lycopene mixture to precipitate a solid lycopene fraction is at a pH of less than 4.

3. The method of claim 2, further comprising separating the solid fraction from the liquid fraction.

4. The method of claim 1, wherein the first enzyme further includes pectinase.

5. The method of claim 1, wherein the pH of the first enzyme treated mixture is in the range of about 3.5 to about 5.

6. The method of claim 1, further comprising filtering the first enzyme treated mixture and recovering a liquid fraction of the first enzyme treated mixture.

7. The method of claim 6, further comprising acidifying the liquid fraction of the first enzyme treated mixture to precipitate a solid fraction from the liquid fraction.

8. The method of claim 7, further comprising separating the solid fraction from the liquid fraction.

9. The method of claim 7, further comprising treating the solid fraction with a second enzyme to create a second enzyme treated mixture, wherein the second enzyme includes protease.

10. The method of claim 9, wherein the pH of the second enzyme treated mixture is in the range of about 8 to about 10.

11. The method of claim 9, further comprising acidifying the second enzyme treated mixture to precipitate a solid fraction.

12. The method of claim 1, wherein the method does not include using a lipophilic solvent to separate lycopene.

13. A method of extracting lycopene from plant material, the method comprising:
    (a) acquiring plant material including lycopene and treating the plant material to substantially dissolve the lycopene and create a substantially dissolved first enzyme lycopene mixture;
    (b) treating the lycopene with a first enzyme to create a first enzyme treated mixture and precipitating the lycopene and removing an enzyme extracted lycopene liquid phase from the first enzyme treated mixture to obtain a remainder first enzyme solid phase treated mixture;
    (c) treating the first enzyme solid phase treated mixture to substantially dissolve the lycopene and create a substantially dissolved first enzyme lycopene mixture; and
    (d) treating the substantially dissolved first enzyme lycopene mixture with a second enzyme to create a second enzyme treated mixture different from the first enzyme treated mixture, wherein the second enzyme is different from the first enzyme.

14. The method of claim 13, wherein the first and second enzymes may be selected from the group consisting of cellulase, pectinase, and protease.

15. The method of claim 13, wherein the method does not include using a lipophilic solvent to separate lycopene.

16. A method of extracting lycopene from plant material using enzymes, the method comprising:
    (a) acquiring plant material including lycopene;
    (b) treating the lycopene with a first enzyme to create a first enzyme treated mixture, wherein the first enzyme includes cellulase;
    (c) separating the first enzyme extracted lycopene from the first enzyme treated mixture;
    (d) treating the first enzyme extracted lycopene with caustic soda to substantially dissolve the lycopene and create a substantially dissolved first enzyme lycopene mixture;
    (e) treating the substantially dissolved first enzyme lycopene mixture with a second enzyme to create a second enzyme treated mixture, wherein the second enzyme is different from the first enzyme and includes protease; and
    (f) separating the second enzyme extracted lycopene from the second enzyme treated mixture, wherein the method does not include using a lipophilic solvent to separate lycopene.

* * * * *